(12) United States Patent
Kleen et al.

(10) Patent No.: US 7,706,854 B2
(45) Date of Patent: Apr. 27, 2010

(54) DEVICE FOR RECORDING CROSS-SECTIONAL IMAGES

(75) Inventors: Martin Kleen, Furth (DE); Marcus Pfister, Bubenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 908 days.

(21) Appl. No.: 11/410,631

(22) Filed: Apr. 25, 2006

(65) Prior Publication Data

US 2006/0239531 A1    Oct. 26, 2006

(30) Foreign Application Priority Data

Apr. 26, 2005    (DE)    ........................ 10 2005 019 369

(51) Int. Cl.
*A61B 5/05*    (2006.01)
(52) U.S. Cl. ........................ 600/407; 600/437; 600/462; 600/466; 600/467
(58) Field of Classification Search ................. 600/437, 600/436, 423, 478, 476, 473
See application file for complete search history.

(56) References Cited

U.S. PATENT DOCUMENTS 4,917,097 A * 4/1990 Proudian et al. ............ 600/463
6,134,003 A * 10/2000 Tearney et al. .............. 356/479
6,162,179 A * 12/2000 Moore ........................ 600/466

FOREIGN PATENT DOCUMENTS

EP            713678 A1 * 5/1996
WO    WO 97/32182 A1    9/1997

OTHER PUBLICATIONS

P. Mohana Shankar, "Speckle Reduction in Ultrasound B-Scans Using Weighted Averaging in Spatial Compounding", IEEE Transactions on Ultrasonics, Ferroelectrics, and Frequency Control, Nov. 1986, pp. 754-758, vol. UFFC-33, No. 6.

* cited by examiner

*Primary Examiner*—Long V Le
*Assistant Examiner*—Joel F Brutus

(57) ABSTRACT

In order to improve the quality of cross-sectional images, which have been recorded along a longitudinal axis of a vessel of a body, it is proposed to add successive cross-sectional images to an overall cross-sectional image. Artifacts in the cross-sectional images are hereby weakened and pathological structures to be detected are high-lighted.

7 Claims, 3 Drawing Sheets

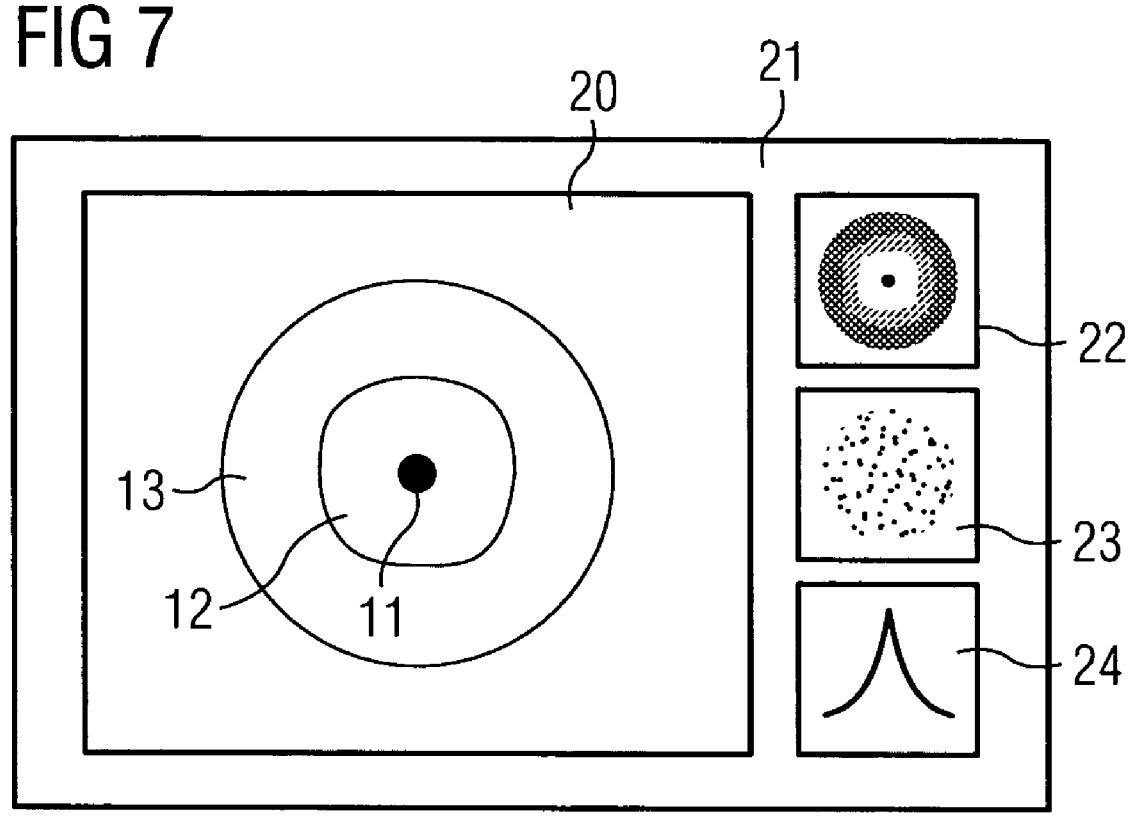

DEVICE FOR RECORDING CROSS-SECTIONAL IMAGES

CROSS REFERENCE TO RELATED APPLICATIONS

This application claims priority to the German Application No. 10 2005 019 369.2, filed Apr. 26, 2005 which is incorporated by reference herein in its entirety.

FIELD OF INVENTION

The invention relates to a device for recording cross-sectional images of the surroundings of a lumen formed in a body, using a probe unit, which comprises a probe which can be inserted into the lumen and a processing unit arranged downstream of said probe, which produces a series of cross-sectional images from the measurement information supplied by the probe unit.

BACKGROUND OF INVENTION

A device of this type is known from WO 97/32182 A1. The known device uses optical coherence tomography to produce cross-sectional images of vessels. In the simplest case, the probe unit of the device features a probe which represents the measuring arm of an interferometer. The probe unit further comprises a reference arm, the optical path length of which can be varied. Light, which features a short coherence length, is fed into both the reference arm and into the measuring arm. The light fed into the measuring arm passes through the probe and is guided to the vessel wall in the region of the probe tip which is located in the vessel to be examined. There the light in different tissue depths is reflected back to the probe tip, detected there and led back through the probe. The light passing back in the reference arm and in the measuring arm is superimposed and supplied to a detector. Modulation means are provided in the reference arm or in the measuring arm, by means of said modulation means the light can be modulated. When the light passing pack from the reference arm and from the measuring arm is interfered in the detector, the intensity detected by the detector is modulated by this modulation. Interference only occurs however when the optical path length of the light in the reference arm and in the measuring arm is approximately the same. By varying the optical path length in the reference arm across several coherence lengths, the photons reflected in each case in a specific tissue depth can result in interference. The probe can be designed such that a cross-sectional profile can be recorded in each instance at a position in the vessel. In the simplest case, this is effected by rotating the probe, with a depth profile being established in each instance in each angular position.

The processing unit arranged downstream of the probe unit then establishes a cross-sectional profile from the measuring signal supplied by the probe unit. As the probe is moved step-by-step through the vessel, the processing unit supplies a series of cross-sectional images one after the other.

SUMMARY OF INVENTION

As the known device is used to carry out vessel examinations on living patients, the intensity of the light fed into the measuring arm is restricted.

Furthermore, only a fraction of the intensity which meets the vessel walls is reflected back to the probe. This results in the cross-sectional images supplied by the known device generally being subjected to significant noise. In addition, the quality of the cross-sectional images depends significantly on whether blood remains in the vessel to be examined or whether the existing blood could be completely rinsed out for the examination. Besides the noise, the cross-sectional images are thus still frequently subjected to significant artifacts.

Both result in the doctor, who is looking for pathological structures in the cross-sectional images, frequently not detecting these or only insufficiently so. Even greater difficulties occur with the detection of pathological structures, if a computer-aided automatic evaluation method is used. A method of this type then requires some degree of interference-free images.

SHANKAR, P. M.: Speckle Reduction in Ultrasound B-Scans Using Weighted Averaging in Spatial Compounding, in IEEE Transactions on Ultrasonics, Ferroelectrics, and Frequency Control. 1986, Vol. UFFC-33, No. 6, pages 754 to 758 further discloses adding cross-sectional images recorded by means of ultrasound for noise reduction purposes to an overall cross-sectional image. To this end, cross-sectional images from different directions are recorded from a target region and the recorded cross-sectional images are averaged into an overall cross-sectional image.

Based on this prior art, an object underlying the invention is to specify a device which supplies cross-sectional images with improved image quality.

This object is achieved by a device with the features of the independent claim. Advantageous embodiments and developments are specified in the claims dependent thereon.

The device is characterized in that the processing unit adds the cross-sectional images recorded by the probe at different positions of a longitudinal axis of the lumen to an overall cross-sectional image. Since the image artifacts generated by residual blood feature considerably smaller dimensions than the pathological structures to be found, an addition of cross-sectional images recorded from along the path of the probe in the lumen weakens the image artifacts and highlights the pathological structures. In addition, the image noise is reduced. Both result in the diagnosis being essentially facilitated for the treating doctor and the use of automatic evaluation methods being made possible.

With a preferred embodiment, the processing unit adds cross-sectional images which have been recorded along a stretch, the lengths of which correspond to the size of a pathological structure to be detected. In this way, artifacts are most effectively suppressed and the pathological structures sought are most effectively highlighted.

With a further preferred embodiment, the processing unit executes a weighted addition of the individual cross-sectional images. This allows artifacts to be particularly effectively suppressed and allows pathological structures to be particularly clearly highlighted.

By way of example, the central image can be weighted most heavily in the case of an addition. This prevents image structures from changing erratically and only being localized with difficulty.

In addition, it is possible for the processing unit to weight central images to a lesser degree than images which are located at the edge of the series of cross-sectional images to be added. This allows artifacts, which are located in the central cross-sectional images, to be intentionally suppressed.

With a preferred embodiment, the number of images to be added and the type of weighting can be adjusted by a user. This is advantageous in that the number of images to be added and the type of weighting can be adjusted to the size and structure of the pathological structure to be detected.

Finally, it is also advantageous if the processing unit is able to consider differential images between the overall cross-sectional image and one or a number of cross-sectional images. On the basis of the differential images, the user is able to detect whether the processing unit is using the suitable weighting and whether the processing unit is adding a suitable number of individual cross-sectional images.

The device is, in particular, a device for examining vessels with the aid of optical coherence tomography. In addition, the device can however also be used in conjunction with the intravascular ultrasound diagnostics.

BRIEF DESCRIPTION OF THE DRAWINGS

Further details and advantages of the invention emerge from the description below, in which exemplary embodiments of the invention are described in detail with reference to the appended drawing, in which;

FIG. 7 shows a screen view of a processing unit for cross-sectional images.

DETAILED DESCRIPTION OF INVENTION

Figure 1:
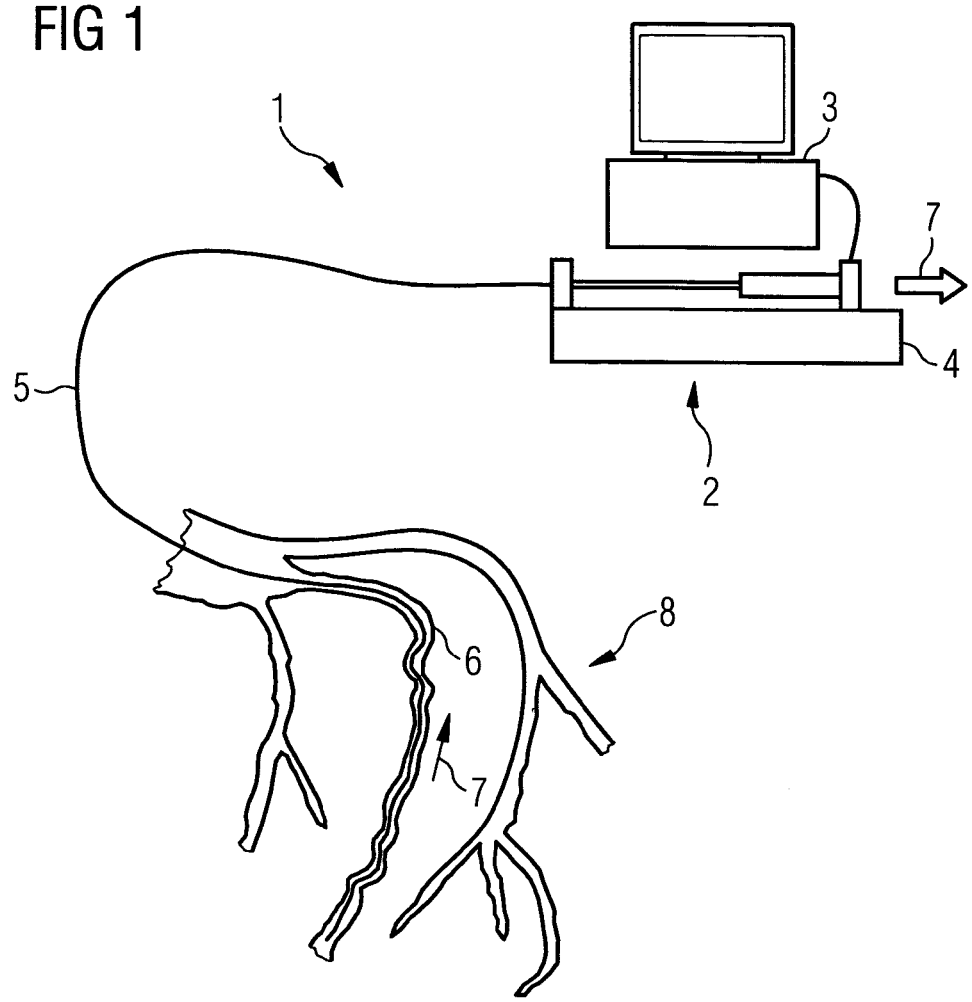
FIG. 1 shows a device for recording cross-sectional images of a vessel.

FIG. 1 shows an optical tomography device 1 with a probe unit 2 and a processing unit 3. The processing unit 3 can be a computer for instance, which is able to digitize and further process the analog signals supplied by a detector of the probe unit 2 as a result of a suitable plug-in card.

FIG. 1 only shows a pulling tool 4 of the probe unit 1, with the aid of said pulling tool a catheter 5 can be withdrawn from a vessel 6 in a pull direction 7. For this purpose, the catheter has been first inserted into the vessel 6. The vessel 6 can be a part of a vascular tree 8 of the heart for instance.

Figure 2:
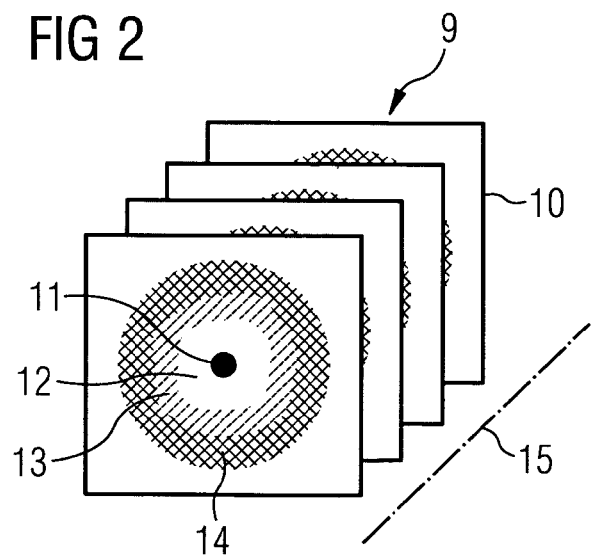
FIG. 2 shows a series of cross-sectional images recorded during the examination of a vessel.

Whilst the catheter 5 is withdrawn from the vessel 6, the optical tomography device 1 produces a series 9 of cross-sectional images 10, which are shown in FIG. 2. The cross-sectional images 10 each show a catheter cross-section 11 and a vessel lumen 12, which is surrounded by a vessel wall 13. A part of the vessel 14 surrounding the vessel wall 13 is also shown.

The cross-sectional images 10 are produced in a known manner with the aid of the probe unit 2 and the processing unit 3. The means required for this purpose are known to the person skilled in the art and are as such not the subject-matter of the application.

Figure 3:
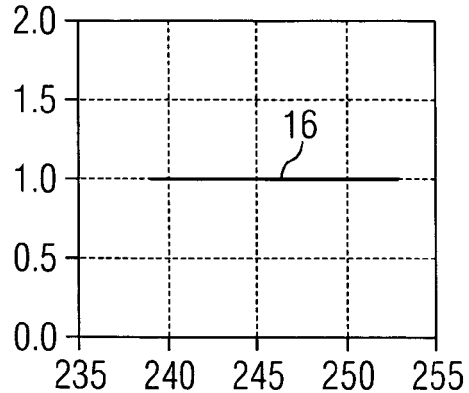
FIG. 3 to 6 show diagrams, in which different possibilities of weighting the individual cross-sectional images are displayed.
Figure 4:
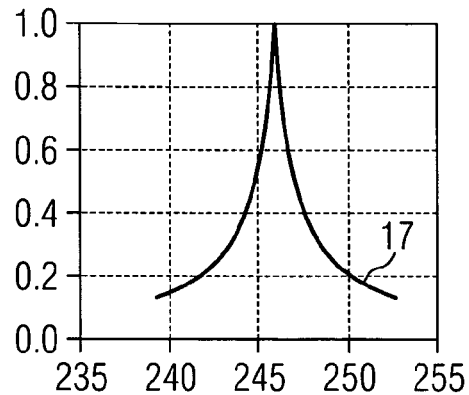
Figure 5:
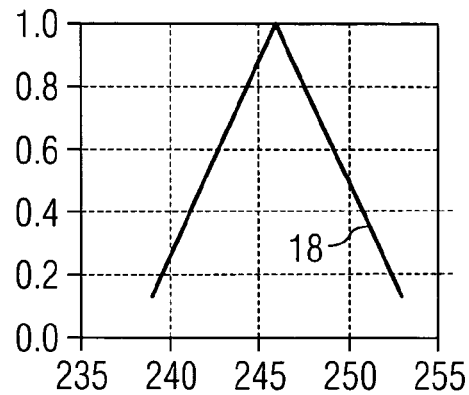
Figure 6:
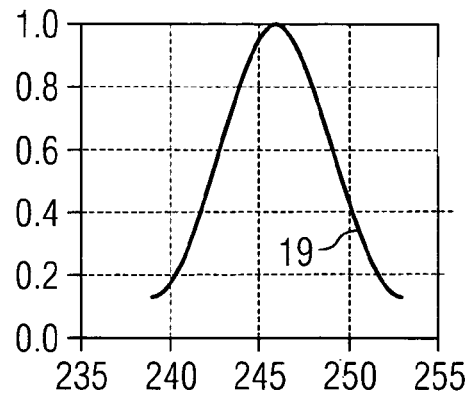

With the optical tomography device 1, the cross-sectional images 10 recorded at different positions along a longitudinal axis 15 of the vessel are added. Different weighting functions are shown in the FIGS. 3 to 6. The continuous number of the cross-sectional images 10 is plotted along the x-axis. The weighting factor assigned to the respective cross-sectional images 10 is plotted along the y-axis. The images are weighted equally in the case of an equal weighting 16 according to FIG. 3. The linear weighting 18 according to FIG. 5 or the Gaussian weighting 19 according to FIG. 6 behave differently to the reciprocal weighting 17 displayed in FIG. 4. With the reciprocal weighting 17, the linear weighting 18 and the Gaussian weighting 19, central cross-sectional images 10 are overweighted. Besides the weightings displayed in FIGS. 3 to 6, other weightings can also be used which underweight the central cross-sectional images 10.

The weighted addition of the cross-sectional images 10 results in a current overall cross-sectional image 20, which can be displayed on a screen 21 of the processing unit 3, as in FIG. 7. Besides the overall cross-sectional image 20 which arises from the addition of several individual cross-sectional images 10, the current central cross-sectional image 22, a differential image 23 as well as a current weighting function 24 are displayed on the screen 21.

The overall cross-sectional image 20 is generated by the processing unit 3 by adding R cross-sectional images 20 prior to the current cross-sectional image 22 and R cross-sectional images 20 after the current cross-sectional image 22, according to the formula:

$$A(i) = \sum_{k=i-R}^{i+R} w(k, R) \cdot F(k) \tag{\#1}$$

with A(i) representing the i-th overall cross-sectional image, w(k,R) the k-th weighting factor of a weighting of the width 2F and F(k) the k-th cross-sectional image 10.

The individual weighting functions are preferably standardized, so that:

$$\sum_{k=i-R}^{i+R} w(k, R) = 1 \tag{\#2}$$

Furthermore, the weighting functions are preferably symmetrical in relation to the central cross-sectional image 22 and feature the greatest weighting factor there.

The number of cross-sectional images 10 to be added or the width of the current weighting function 24 should be selected such that the added stack of cross-sectional images 10 extends across a stretch along the vessel 6, the length of which corresponds somewhat to the size of the pathological structure to be detected. By the addition, artifacts in the cross-sectional images 10 are weakened and pathological structures are amplified, so that these appear essentially more clearly in the overall cross-sectional image 20 than in the individual cross-sectional images 10.

The weightings 17 to 19 centered on the current cross-sectional image 22 and constantly decreasing from there are advantageous in that no erratic image changes occur. An artifact contained in a cross-sectional image 10 can thus not result in a sudden change in the overall cross-sectional image 20. Conversely, an artifact contained in the current cross-sectional image 22 is also not averaged to such an extent as with the equal weighting 16.

A weighting, which underweights the central current cross-sectional image 22, is particularly suitable when the spatial positions of the artifacts are known or when gaps appear, which are to be taken out from the sequence of cross-sectional images 10 used for the overall cross-sectional image 20.

To prevent the information getting lost as far as possible by averaging the cross-sectional images 10, the differential image 23 is displayed on the screen 21, said differential image 23 containing the differential values between the current overall cross-sectional image 20 and the current cross-sectional image 22. If regular structures are detected in the differential image 23, this indicates a weighting function which is too wide or a centrally loaded weighting which is too low.

The processing unit 3 thus preferably offers the user the possibility of adapting the used weighting function. In this case, the user is particularly able to adjust to the type of weighting function, as well as its parameters. Furthermore, the user is able to select one of the cross-sectional images 10 from sequence 9 as a current central cross-sectional image 22 and is thus able to determine the position of the stack of the averaged cross-sectional images 10 and add them to the current overall cross-sectional image 20.

The optical tomography device 1 generally provides an essentially clearer image of the vessel 6 to be examined than conventional optical tomography devices. In addition to the catheter cross-section 11, which is, as a rule, also clearly detectable in the cross-sectional images 10, the vessel lumen 12 and the vessel wall 13 can be detected in a clearly differentiated manner.

It is worth noting, that the catheter cross-section 11 in the individual cross-sectional images 10 is generally used to additionally apply the individual cross-sectional images 10 for coverage purposes.

The medical diagnosis is essentially facilitated using the optical tomography device 1. Furthermore, consideration can be given to using automatic, computer-aided diagnosis methods.

To conclude, it is worth noting that the concept described here of the processing of cross-sectional images 10 can also be applied in intravascular ultrasound images, which have been recorded with the aid of an intravascular ultrasound device.

The invention claimed is:

1. A device for recording cross-sectional images of an area surrounding a lumen formed in a body, comprising:
   a probe unit having a probe sized and configured to be inserted into the lumen; and
   a processing unit connected to the probe unit, the processing unit configured to generate a sequence of cross-sectional images based on measuring information acquired by the probe unit along a longitudinal axis of the lumen, wherein the processing unit is configured to add up the generated cross-sectional images to form a cumulative cross-sectional image,
   wherein the generated cross-sectional images include a designated central cross-sectional image, and the processing unit is further configured to calculate and display a differential image based upon the central cross-sectional image and the cumulative cross-sectional image.

2. The device according to claim 1, wherein the generated cross-sectional images are weighted by the processing unit before being added up.

3. The device according to claim 2, wherein the generated cross-sectional images include a central cross-sectional image, and the generated cross-sectional images are weighted the stronger the closer they are located relative to the central cross-sectional image.

4. The device according claim 2, wherein the generated cross-sectional images include a designated central cross-sectional image, and the generated cross-sectional images are weighted the stronger the further away they are located relative to the central cross-sectional image.

5. The device according to claim 2, wherein weighting the generated cross-sectional images includes assigning weighting parameters to the generated cross- sectional images by a user.

6. The device according to claim 1, wherein the device is an optical tomography device.

7. The device according to claim 1, wherein the device is an intravascular ultrasonic device.

* * * * *